United States Patent [19]

Wiland et al.

[11] 4,158,256

[45] Jun. 19, 1979

[54] DETACHABLE FASTENER FOR A DENTAL CAP AND PROSTHODONTIC METHOD UTILIZING THE SAME

[75] Inventors: Lawrence Wiland, 42-45 Kissena Blvd., Queens, New York, N.Y. 11355; Robert Humphrey, 227 Corlies Ave., Pelham, N.Y. 10803; Peter Consiglio, Lindenhurst, N.Y.

[73] Assignees: Lawrence Wiland, Queens; Robert Humphrey, Pelham, both of N.Y.

[21] Appl. No.: 815,173

[22] Filed: Jul. 13, 1977

[51] Int. Cl.² .............................................. A61C 5/08
[52] U.S. Cl. ...................................................... 32/12
[58] Field of Search .......................... 32/2, 12, 8, 13, 5, 32/6

[56] References Cited

U.S. PATENT DOCUMENTS

| | | | |
|---|---|---|---|
| 3,514,859 | 6/1970 | Peterson | 32/2 |
| 3,787,975 | 1/1974 | Zuest | 32/5 |
| 3,797,114 | 3/1974 | Wiland | 32/12 |

*Primary Examiner*—Robert Peshock

*Attorney, Agent, or Firm*—Mark T. Basseches; Paula T. Basseches

[57] ABSTRACT

An arrangement and a method of prosthetically repairing teeth includes preparing a tooth by marking major surfaces thereof with scribe lines, and by removing tooth structure from the tooth in dependence upon the location of the scribe lines. An elongated recess is formed in the prepared tooth. A coping adapted for placement over the prepared tooth fits in the recess and is formed with a bore which extends in direction of the elongation of the recess. An artificial crown or cap adapted for placement over the coping is formed with a cavity which extends in direction of the elongation of the recess. A two-part detachable fastener has one part mounted in the bore of the coping and its other part mounted in the cavity of the cap. The mutual alignment of the bore and the cavity permits the cap to be secured to the coping with little play when the fastener parts are moved into fitting engagement with each other. The detachable fastener may be of snap-type or of magnetic-type.

13 Claims, 17 Drawing Figures

DETACHABLE FASTENER FOR A DENTAL CAP AND PROSTHODONTIC METHOD UTILIZING THE SAME

BACKGROUND OF THE INVENTION

1. Field of the Invention

The present invention relates generally to a prosthodontic method of repairing one or more teeth in a patient's mouth and, more particularly, to a miniature detachable fastener which is located within the confines of an artificial crown and a coping. The fastener is installed within each tooth to be repaired pursuant to such method.

2. Description of the Prior Art

In the art of dental prosthesis, it is known to prepare a tooth in need of major prosthodontic repair and then to cement an artificial crown or cap on the prepared tooth. A prepared tooth is one which has some or all of its structure removed. Conventionally, the side walls of such prepared teeth are tapered upwardly for a lower tooth and downwardly for an upper tooth such that such teeth have a generally frusto-conical configuration. This configuration facilitates the secure mounting of a coping over the prepared tooth, as well as the mounting of the cap over the coping.

The permanent attachment of a cap either directly on the tooth or on the coping is highly unsatisfactory because once the cap is permanently emplaced, it is not easy to replace it in order to modify or correct an occlusion. Such permanent emplacement also makes it very difficult to remove the cap without causing damage to the cap and/or the tooth and/or the surrounding gingival tissue. Moreover, it is very difficult to thoroughly clean and maintain this gingival tissue healthy.

In another type of dental prosthesis, it is known to prepare teeth at the ends of a gap caused by extraction of one or more teeth. These prepared end teeth serve as anchors for two caps provided at opposite ends of a bridge structure. A plurality of artificial teeth are interconnected to the two caps. The permanent emplacement of such a bridge structure not only has the drawbacks noted above for the capping of a single tooth, but also permits food particles to enter into the space between the bottoms of the intermediate artificial teeth and the gums. Such food particles are difficult to remove, facilitate the formation of diseased tissue and cause foul odors to form. Massaging and cleaning of the gum tissues likewise become more elaborate.

It is further known in the art to make removable caps and removable bridges. It has been proposed to form a vertical dovetail mortise in a tooth adjacent a gap and to mount a vertical dovetail tenon on a single artificial tooth which then would be held in the gap by a mortise-and-tenon connection. It has been further proposed to provide metal clips or clasps which engage the external surfaces of the patient's teeth adjacent the ends of the gap to be closed by a bridge. Such metal clasps are subject to material fatigue and also place an undue stress upon the engaged teeth.

It is known in U.S. Pat. No. 3,797,114 to mount a two-part detachable fastener partly within the confines of a cap and partly within the confines of a coping which is attached to a prepared tooth. Such detachable fasteners generally overcome the drawbacks noted above; however, they have not proven to be altogether satisfactory in use due to improper alignment of the two parts of the fasteners. Such fasteners are generally of large dimensions and therefore are not well adapted to be easily fitted within the confines of small prepared teeth.

Another prior art proposal for a detachable fastener requires the root of the tooth to be repaired to be as short as possible in order to mount the fastener. In other words, all of the structure of the tooth is removed down to the gingival margin, and even below the same; that is, the entire upper portion of the tooth is ground off leaving only the root embedded in the gums and jawbone. This is very disadvantageous because it constitutes a very radical procedure which tends to shock the patient's physiological system. It will be appreciated that the root of a tooth is considerably more slender than the portion of the tooth above the gingival margin, and that the hard skin of a root is not as thick or as hard as the enamel of a patient's crown. Therefore, when this prior art fastener is mechanically integrated with a patient's tooth, a considerable danger exists for fracture in the root during such mounting and/or during the preparation of the tooth. In extreme cases, once this root is damaged, the dentist must extract the tooth, frequently with considerable suffering to the patient. The dentist must now proceed with securing the fastening means to the jawbone itself. However, this procedure imparts an even greater physiological shock to the patient's system. If the jawbone structure is weak, immeasurable damage occurs.

SUMMARY OF THE INVENTION

Accordingly, it is the general object of the present invention to overcome the disadvantages of the prior art.

It is another object of the present invention to provide a reliable method of prosthetically repairing a tooth which accurately fits the parts of a two-part detachable fastener without mutual misalignment.

It is a further object of the present invention to provide an arrangement for prosthetically repairing a tooth which utilizes a miniature two-part detachable fastener which is simple and inexpensive to manufacture.

Yet another object of the present invention is to prevent slippage or loosening of the parts of the detachable fastener in use.

An additional object of the present invention is to provide a detachable mount for a dental cap which cooperates with a tooth which has been prepared such that a substantial bulk lies above the gingival margin, to thereby permit this prepared tooth to be used while the same is still vital.

Yet another object of the present invention is to provide a detachable mount which is attached to a tooth portion that extends above, and preferably substantially above, the gingival margin to thereby enable the remnant tooth portion to assimilate stresses which may be imparted thereto after the cap is emplaced and secured.

Still another object of the present invention is to provide a method of dental prosthodontics which through the use of the detachable mount creates a removable, securely attached cap or bridge which is indistinguishable from a patient's natural teeth.

In keeping with these objects and others which will become apparent hereinafter, one feature of the invention resides, briefly stated, in a prosthetic method of repairing a tooth which comprises the step of preparing the tooth to be repaired, and the step of forming an elongated recess in the prepared tooth. The method further includes providing a coping for placement over the prepared tooth such that the coping fits into the recess and forming the coping with a bore which extends in direction of the elongation of the recess. A cap is provided for placement over the coping and is formed with a cavity which extends in direction of the elongation of the recess. One part of a two-part detachable fastener is mounted in the bore, whereas the other part is mounted in the cavity. The two parts are moved along said direction into engagement with each other to thereby fasten the cap to the coping free of relative misalignment due to the mutual alignment of the bore and the cavity.

In accordance with the invention, the mutual alignment of the cavity and the bore insures the proper fitting of the two parts of the detachable fastener. These aligned parts are now assured of being interfitted without misalignment and without excessive free play therebetween.

Another significant feature of the invention which overcomes the drawbacks of the prior art is the permanent mounting of each part of the detachable fastener to the cap and to the coping respectively by high energy fusion techniques. A high energy beam, for example a laser or an electron beam, is employed to permanently and immovably weld each part together without the aid of a third or different joining material. When conventional base metal solders or precious or semi-precious solders are employed in soldering or brazing operations, objectionable electropotential effects are generated due to fluids in the oral cavity which serve as electrolytes. This fusion feature avoids the prior art problems associated with threaded or clasp-type connections which loosen over time and also avoid the electro-potential problems which are generated by soldering, brazing or analogous heat-treating operations which employ a joining material.

Still another feature of the invention is the use of magnetic materials to interconnect a cap and a coping. Such materials may be configured as very thin sheets or as buttons respectively received in the aforementioned cavity or bore.

Yet another feature of the invention relates to a novel composition for a metal alloy composition used to constitute each part of a snap-type detachable fastener.

Another important feature relates to the verification and checking at each stage of the method for size, fit, bite, color, alignment or any other characteristic that is functionally required before final installation of the coping and/or the cap is made in the oral cavity. An unsatisfactory coping or cap can therefore be detected in advance in the dental office and/or dental laboratory and corrected if required prior to final installation. The alignment, fit, size and retentive force characteristic of the parts of the fastener can likewise be checked in advance. Final assembly of the cap, coping or fastener is made only after the patient, dentist and laboratory are satisfied.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 13 is a fragmentary enlarged cross-sectional view of the prepared tooth of FIG. 8 after a coping has been cemented over the tooth, after a female half of a detachable fastener has been welded to the coping, after a male half of the fastener has been welded to the crown of FIG. 12, and after the crown has been placed over the coping and snapped into place;

FIG. 15 is a fragmentary cross-sectional view showing another way of magnetically connecting a crown to a tooth;

DESCRIPTION OF THE PREFERRED EMBODIMENTS

Figures 1, 2, 3, 4, 5:
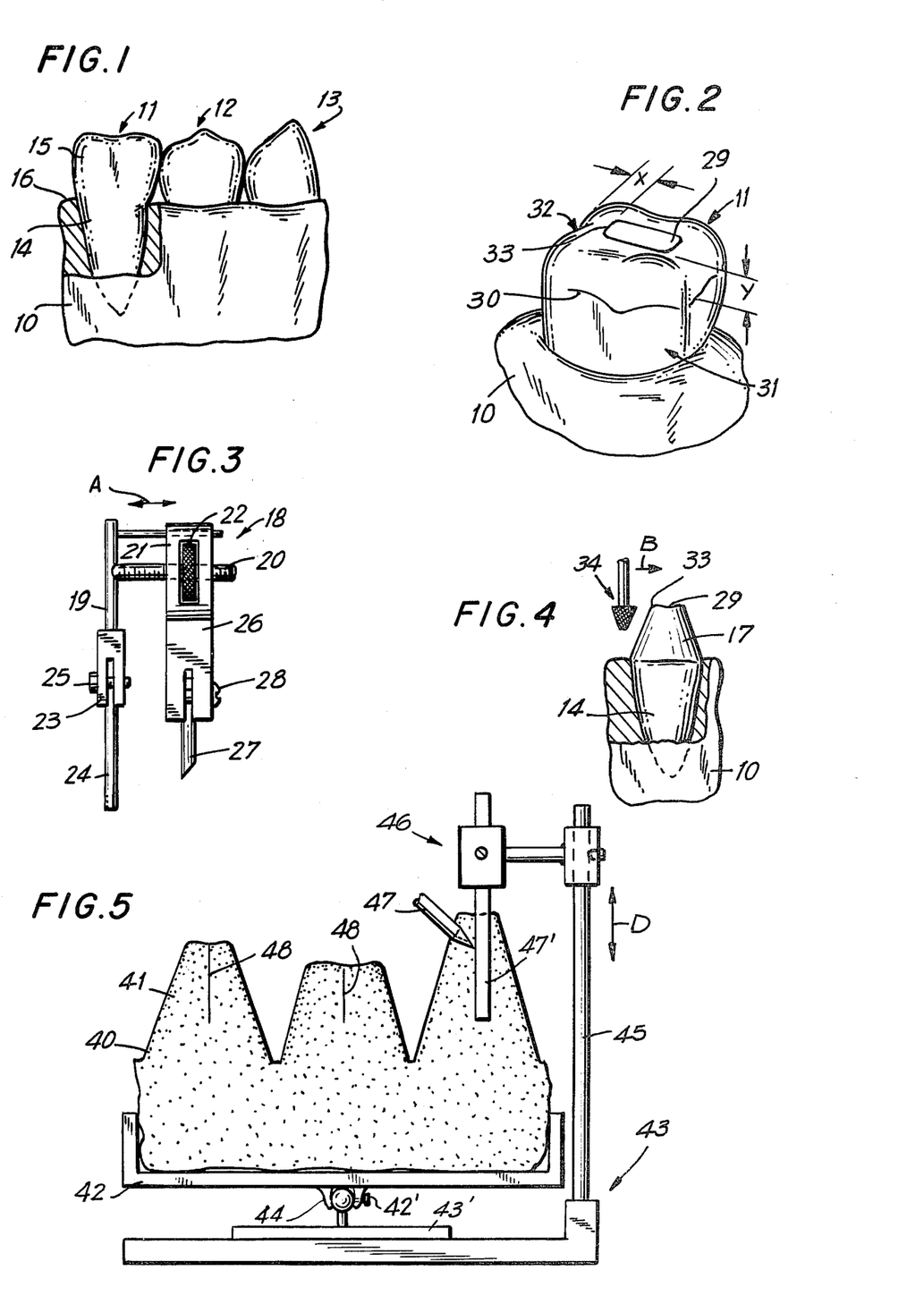
FIG. 1 is a fragmentary elevational view of a patient's mouth showing the labial portions of several adjoining teeth and the adjoining gum, the leftmost one of the teeth being in need of prosthodontic repair pursuant to the method of the present invention, and the gum and bone being partially cut away to show the root of this leftmost tooth.
FIG. 2 is a fragmentary perspective view of the tooth to be repaired after it has been scribed.
FIG. 3 is a side view of a scribing tool used to scribe a tooth as shown in FIG. 2.
FIG. 4 is a fragmentary elevational view of a tooth after it has been prepared pursuant to the method of the invention.
FIG. 5 is a side view of a gypsum mold having a plurality of forms modeled after the teeth to be prepared after the mold has been marked by vertical lines.

Referring now in detail to the drawings and more particularly to FIG. 1, it will be seen that reference numeral 10 identifies a patient's gum in which teeth 11, 12 and 13 are embedded. Teeth 12 and 13 are normal sound teeth and have natural structure which are in satisfactory condition such that no capping is required for these teeth. It will be understood that the crowns of teeth 12 and 13 are not perfect; they may include non-illustrated fillings; or the teeth may be misaligned or discolored or turned or in need of some minor dental repair. However, teeth 12 and 13 have not reached the state wherein complete coverage prosthodontic repair is required.

In contradistinction to teeth 12 and 13, tooth 11 which includes a root 14 and a crown 15 requires capping; for example, tooth 11 may be so badly decayed that only a complete coverage restoration can be made, or tooth 11 may be so badly discolored that the patient requires an artificial crown or cap for cosmetic purposes, or tooth 11 may bound with an adjacent tooth an undesirable space which the patient wishes to span for aesthetic purposes, as well as the functional restoration of a complete dental arch.

In accordance with the method of the present invention, the tooth 11 is "prepared." As used herein, the term "prepare" and its modified forms generally indicate a treatment of a tooth in which some or all of the structure of the crown has been removed, in amount adequate to suit the coping usually but not necessarily to slightly below the gingival margin 16. FIG. 4 shows the tooth 11 after it has been prepared by removing some of its structure such that a substantial residual bulk of the portion of the tooth 11 that formerly underlaid the removed crown structure is left intact in order to leave a considerable mass of the tooth protruding above the gum. Reference numeral 17 identifies the "prepared segment" or upper portion of the tooth 11 which extends from above the gingival margin to below the same as good practice requires. The amount of tooth structure removed should not be more than sufficient to adequately accommodate the wall thicknesses of both the coping and the artificial crown (telescope).

In order to accurately control the amount of tooth structure removed from tooth 11, a measuring and scribing tool 18 as shown in FIG. 3 is employed. Scribing tool 18 comprises a rod holder 19 which is mounted on threaded shaft 20, and a marker holder 21 which is also mounted on shaft 20. A rotary control knob 22 threadedly engages shaft 20 and is operative for moving marker holder 21 relative to rod holder 19 lengthwise of shaft 20 along the to-and-fro direction of double-headed arrow A in order to measure and pre-select a spacing between holders 19 and 21. Rod holder 19 includes support clamp 23 having juxtaposed resilient fingers intermediate which bearing rod 24 is positioned and fixedly clamped by turning support screw 25 in requisite direction. Marker holder 21 includes a support clamp 26 having juxtaposed resilient fingers intermediate which marker 27, preferably a graphite rod, is positioned and fixedly clamped by turning support screw 28 in requisite direction.

In use, one must first determine how much tooth structure as well as where the latter is to be removed from tooth 11. Rather than merely visually inspecting the tooth in situ in the gum, a non-illustrated transparent diagnostic template which has a grid of intersecting lines arranged normally and at measured distances relative to each other is placed over an X-ray photo of the tooth to be prepared. As will be described in greater detail below, an attachment is to be mounted within the interior of the prepared segment 17. These attachments are configured in a plurality of sizes and are diagrammatically represented on the template. Once the properly sized attachment is selected by the template, the practitioner can determine how much tooth structure can safely be removed from the tooth 11 while still leaving sufficient room to later mount the selected attachment.

The rotary knob 22 is turned until the marker 27 is spaced from rod 24 at a predetermined distance which corresponds to the amount of the structure to be removed. The scribing tool 18 is placed in the patient's mouth such that the rod 24 is placed in engagement with one of the major top or side surfaces of the tooth. The practitioner now moves the rod 24 along the selected major surface of the tooth 11, and simultaneously the marker 27 scribes a line along another major surface of the tooth. For example, in FIG. 2 if the rod 24 is moved over top tooth surface 29, then the marker 27 will scribe mark 30 over the side tooth surface identified by reference numeral 31. Mark 30 is spaced at a predetermined distance y below the top surface 29. In addition, if the rod 24 is moved over left side tooth surface 32, then the marker 27 will scribe mark 33 over the top tooth surface 29. Mark 33 is spaced at a predetermined distance x from left side surface 32.

In a completely analogous manner, all major surfaces of the tooth are scribed. The markings serve as reference points and indicate to the practitioner the outermost limits to which tooth-preparing tool 34 is directed. For example, in FIG. 4, tooth-preparing tool 34 is moved in transverse direction of arrow B unit it reaches the mark 33 on top tooth surface 29. Scribing tool 18 is an independent and separate unit, as illustrated, or it may be attached to tool 34. The vital tooth is shaped by grinding tools so that enough structure is removed to accommodate the wall thickness of the coping and the cap. Such thicknesses will vary at different locations on the teeth, both for anterior teeth (incisors and canines) as well as posterior teeth (premolars and molars), and will also vary according to what materials are used to constitute the cap and/or coping. For example, the cap may be constituted solely to be metal material, or be a combination of metal and ceramic (e.g. porcelain) materials, or be a combination of metal and synthetic plastic materials, just to mention a few possibilities.

The finished tooth segment is generally one and one-half times higher than its width at the base. The taper or angle of inclination at the sides of the tooth is on the order to 5° to 7°. The drawings are not drawn on a 1:1 scale for purposes of showing details in enlarged view.

Figure 8:
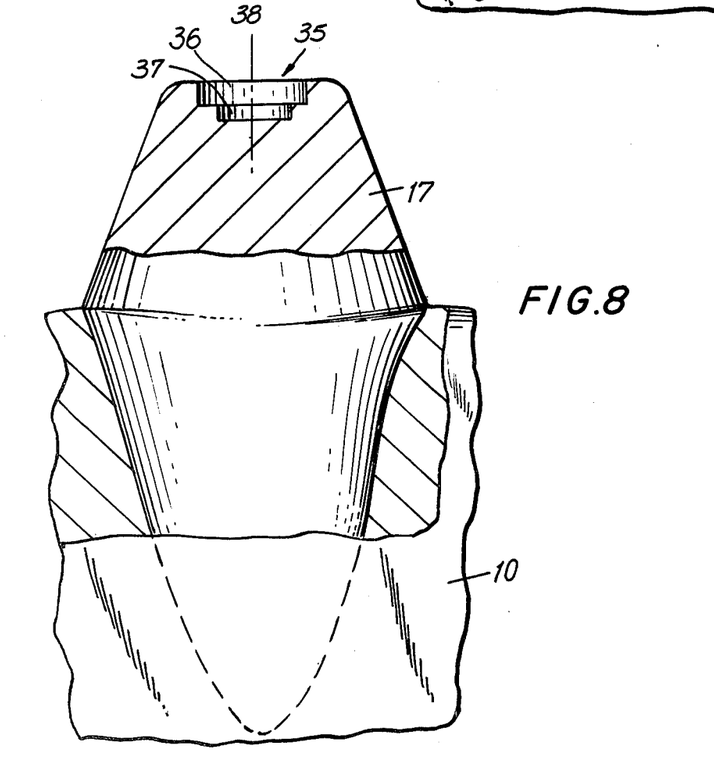
FIG. 8 is a fragmentary partially sectional view of a prepared tooth with a recess pursuant to the method of the invention.

After preparation of the tooth 11 has been completed, the method next provides for forming a counterbore or recess 35 in prepared segment 17 as shown in FIG. 8. In order to assure that the elongation of recess 35 is along the true vertical, i.e. in direction of vertical axis 38, the practitioner is once more provided with a guide to assist him in properly aligning the structure-removing tool 39 in the patient's mouth.

Such proper alignment is obtained by first taking an impression of all of the teeth in the patient's mouth. A molding substance such as alginate is applied over the teeth in conventional manner. Gypsum is poured into the hardened alginate. The gypsum subsequently hardens to form a mold 40 which is an accurate model of the teeth in the patient's mouth. Gypsum model 40 in FIG. 5 shows three models of such teeth; the actual number of such models depends, of course, upon the particular application. For the sake of this discussion, model form 41 is an accurate copy of prepared tooth segment 17.

The gypsum model 40 is placed on tilt table 42 of support stand 43. Universal ball joint 44 permits the table 42 to be tilted to and locked by screw 42' in a position such that all of the model forms are elongated generally in vertical direction. A marking tool 46 which includes vertical shaft 47' is mounted on vertical post 45. Marker 47 is manually moved along shaft 47' in direction of the double-headed arrow D. The marker 47 is operative for marking the model forms with a vertical guideline, as identified by lines 48 in FIG. 5. Plate 43' slides on stand 43.

Figure 6:
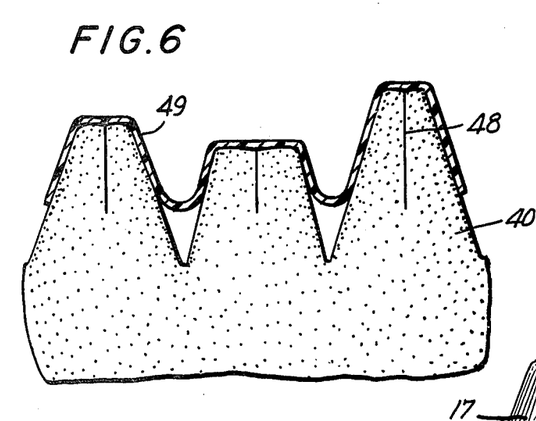
FIG. 6 is a side view of the mold of FIG. 5 and a sectional view of a transparent plastic envelope which has been vacuum-formed over the model forms of the gypsum mold.

The thus marked gypsum model 40 is now placed underneath a transparent planar thermoplastic sheet in a chamber of a conventional vacuum-forming machine. The thermoplastic sheet is subjected to heat, and then placed directly above the model forms of gypsum model 40. A suction source is now connected to the underside of the heated sheet and is operative for drawing the softened sheet downwardly into direct intimate contact with the model forms so as to form the transparent plastic envelope identified in FIG. 6 by reference numeral 49.

Figure 7:
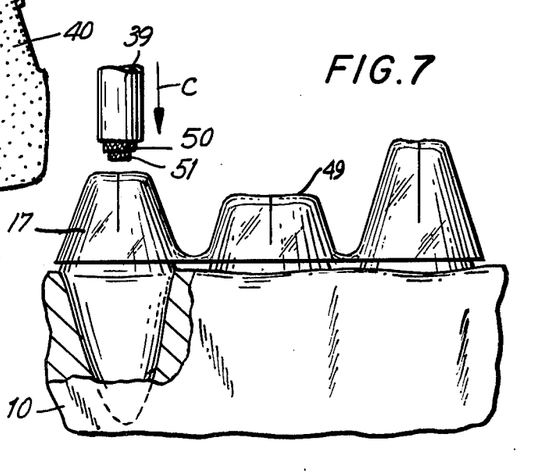
FIG. 7 is a view of the plastic envelope after it has been placed over the prepared teeth in a patient's mouth, the envelope serving as a guide for a tooth-preparing tool.

The guidelines 48 on gypsum model 40 are visible through envelope 40 and serve as guides for one to mark corresponding guidelines directly on the outer side of the envelope 49. The thus marked envelope 49 is now placed in the patient's mouth over the patient's prepared teeth. The guidelines which are now marked on the envelope 49 serve as a guide for the structure-removing tool 39. A practitioner merely guides tool 39 along the respective vertical line to form recess 35 in the desired proper alignment with vertical axis 38.

Recess 35 is comprised of larger bore portion 36 and smaller coaxial bore portion 37. These two bore portions can be formed by the single tool 39 having combined drill bit portions 50 and 51. Bit portions 50, 51 correspond to bore portions 36, 37, respectively. Alternatively, two different tools may be employed, each tool having a roughened bit portion which corresponds to either bit portion 50 or bit portion 51.

The next step according to the method of the present invention is to make a coping of any shape-retaining coping material, such as metal, ceramic or synthetic plastic material, for permanent attachment over the prepared tooth segment 17. The coping is fabricated by first taking another impression, a so-called master impression, by applying rubber or silicone material over the patient's prepared teeth which now are formed with recess 35. Gypsum is poured into the hardened master impression to form master mold 52. Master mold 52 having representative model form 66 is placed on tilt table 53 of a support stand 54 and locked in position by screw 53'. Upright shaft 55 is oriented in the same vertical direction as shaft 45 of the support stand 43 illustrated in FIG. 5. In fact, it is advantageous to use this same support stand to insure proper vertical orientation. Plate 54' slides on stand 54.

Figure 9:
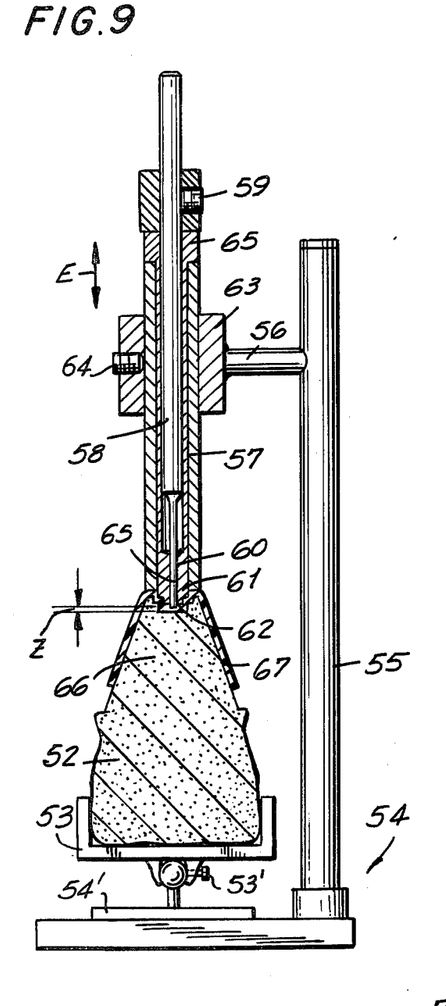
FIG. 9 is a side view of a fragmentary master mold having a model form coated with wax, the thickness of the wax being controlled by a depth gauge arrangement.

Horizontal arm 56 has one end fixedly mounted on shaft 55, and its opposite end fixedly mounted on stationary collar 63. Outer sleeve 57 is mounted in collar 63 for vertical sliding movement relative to the latter along the double-headed arrow E. Set screw 64 is turnable in requisite direction to arrest such sliding movement of sleeve 57. An intermediate sleeve 60 is mounted in outer sleeve 57 for vertical sliding movement relative to the latter. Abutment shoulder 65 is engageable with the upper trailing end face of sleeve 57 to thereby arrest such sliding movement of intermediate sleeve 60. The lower end region of intermediate sleeve 60 has larger shaft portion 61 and smaller shaft portion 62; the dimensions of shaft portions 61, 62 correspond generally to recesses 36, 37, respectively. A depth gauge rod 58 is mounted in intermediate sleeve 60 for vertical sliding movement relative to the latter. Set screw 59 is turnable in requisite direction to arrest such sliding movement of rod 58.

After the master mold 52 is placed on tilt table 53, the outer sleeve 57 and depth rod 58 are both lowered until the leading end face or tip 65 of rod 58 engages the bottom wall of recess 37. Set screws 64 and 59 now fix the position of outer sleeve 57 and rod 58, respectively. The leading end face of shaft portion 62 is now spaced at a predetermined distance z from the bottom wall of recess 37. Similarly, the leading end face of shaft portion 61 is also spaced at this predetermined distance z from the bottom wall of recess 36. The diameter of each shaft portion 61 and 62 is 2 z smaller than its associated recesses 36, 37.

The intermediate sleeve 60 and the rod 58 are now retracted upwardly through outer sleeve 57. Investment-casting wax or any acrylic resin is now applied over model form 66. Thereupon, the intermediate sleeve 60 is relowered, and its shaft portions 61, 62 deform and shape the wax coating such that a substantially uniform thickness z of wax coats the entire inner circumferential wall bounding the recess 35.

Figure 10:
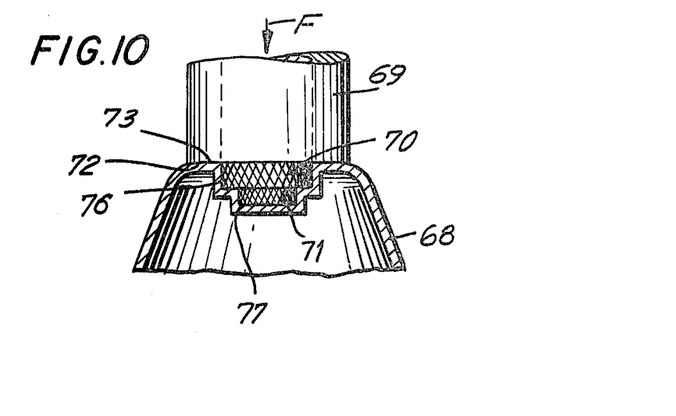
FIG. 10 is a side view of a fragmentary metal coping and of a metal-removing tool operative for forming bore sections in the coping.

The hardened wax coating 67 is now ready to be investment cast by known investment molding techniques. Typically, a ceramic powder liquid wash such as silicon dioxide powder is applied over the wax coating 67 and allowed to harden. A heated metal, such as a gold alloy, is admitted into the hardened ceramic mold. The metal melts and changes places with the wax coating. As shown in FIG. 10, the finished metal coping 68 is a substantially exact duplicate of the wax coating 67.

The next step in accordance with the present invention is to position a stud 75 at the top region of the coping 68. First, the top surface 72 of the coping 68 is faced off, i.e. machined to a substantially planar configuration. The exterior of the coping 68 is advantageously scraped or otherwise machined to obtain a final desired uniform wall thickness, preferably on the order of 0.25 to 0.40 mm. Next, a material-removing tool 69 having a shoulder 73 and a combined drill bit comprised of larger drill bit portion 70 and smaller drill bit portion 71 is advanced along the direction indicated by arrow F in FIG. 10 until shoulder 73 abuts against planar top surface 72. Bit portions 70, 71 remove material and are operative to size bore sections 76 and 77 to their final desired dimensions. A single tool 69 need not be used; two separate tools each having a respective bit portion corresponding to either bit portion 70 or 71 may be equivalently employed.

Figure 11:
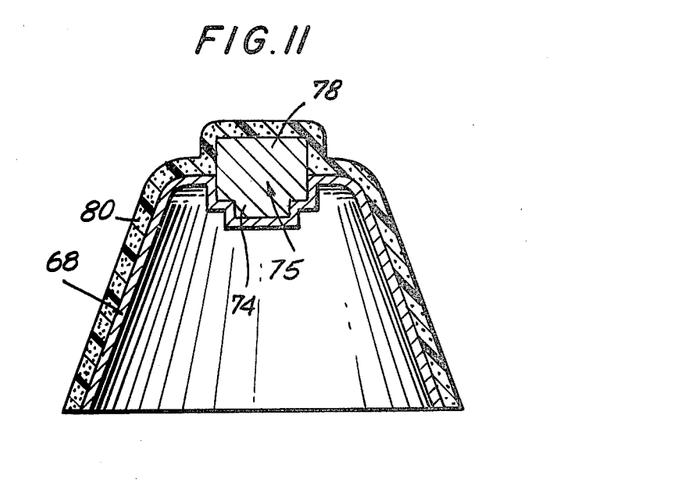
FIG. 11 is a fragmentary cross-sectional view of a coping after a stud has been inserted into its bore sections and after a wax coating has been applied.

Upon removal of tool 69, lower portion 74 of stud 75 is inserted into the bore sections 76, 77. Upper portion 78 of stud 75 extends above the top surface 72 of the coping 68.

Figure 12:
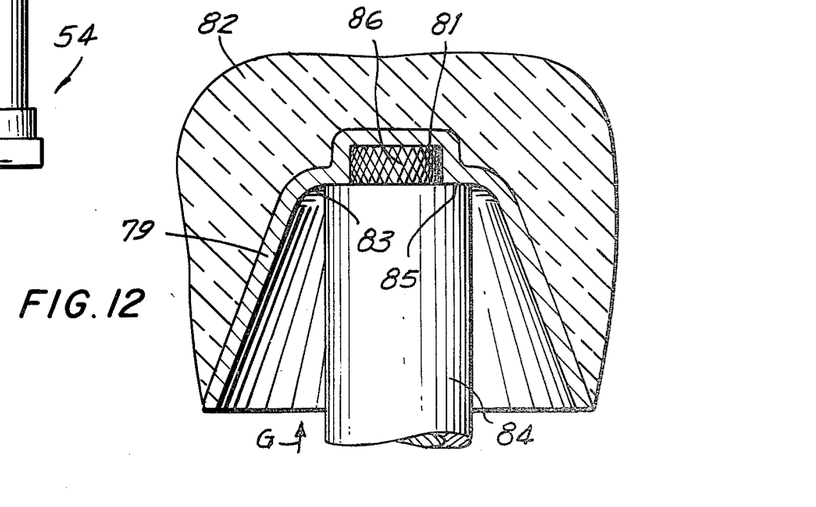
FIG. 12 is a fragmentary cross-sectional view of an artificial metal crown and a metal-removing tool operative for forming a cavity in the crown.

The next step in accordance with the invention is to fabricate an artificial crown or cap as identified by reference numeral 79 in FIG. 12. The cap 79 is fabricated by first applying a wax overcoat 80 or any other analogous molding material over the coping 68 and over the stud 75 mounted in the latter and allowing the wax to harden. Upon removal of the wax overcoat 80 from the coping 68, the interior is now formed with a counterbore or cavity 81 due to the previous presence of the upper portion 78 of stud 75.

Again, investment-casting techniques are employed to substitute any shape-retaining material, such as metal, (e.g. a gold alloy), for the wax overcoat 80 which is illustrated as a thin-walled shell. For cosmetic purposes, a ceramic or synthetic plastic material or porcelain coating 82 may be deposited over cap 79 and is shaped to resemble the natural tooth structure. The wax overcoat 80 need not be a shell but may be shaped to resemble the outer contour of a natural crown. In this case, after substitution of metal, for example, for the wax is accomplished, the cap is a one-piece structure entirely constituted by metal.

The cap 79 is finished by first facing off the inner surface 83 to a substantially planar configuration. Next, a material-removing tool 84 having a shoulder 85 and drill bit portion 86 is advanced along the direction indicated by arrow G in FIG. 12 until shoulder 85 abuts against planar surface 83. Drill bit portion 86 machines the cavity 81 to its final desired dimensions.

Figures 14, 16, 17:
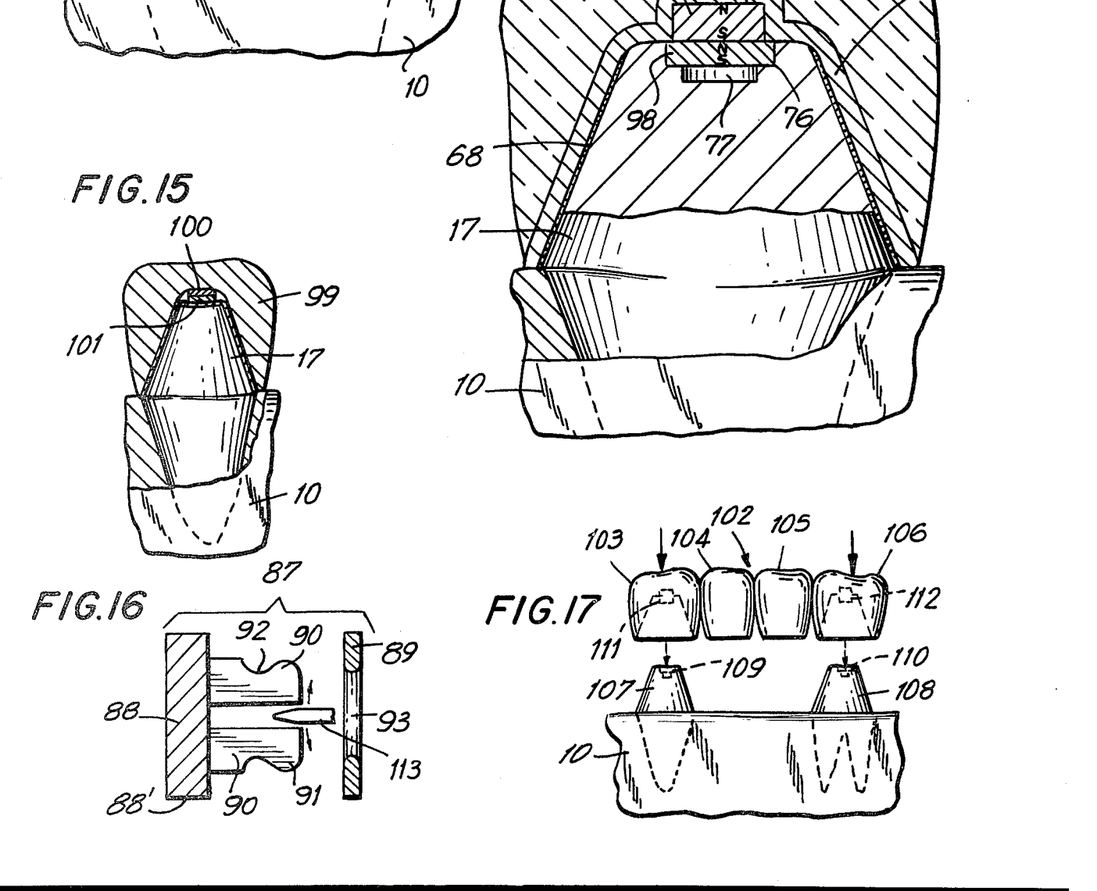
FIG. 14 is a fragmentary cross-sectional view analogous to FIG. 13 but showing magnetic means for detachably fastening the crown to the coping.
FIG. 16 is an enlarged cross-sectional view of the detachable fastener employed in the embodiment of FIG. 13.
FIG. 17 is a fragmentary partially diagrammatic view of a bridge structure for detachable mounting to anchor teeth in accordance with the present invention.

At this stage, the practitioner has metal cap 79 formed with an interior socket which matches the exterior of the coping and which has an interior cavity 81 as shown in FIG. 12, and he further has metal coping 68 formed with bore sections 76, 77 after stud 75 has been removed from these bore sections. In accordance with the next step of the method of the invention, detachable fastening means of attachment 87 having a male portion 88 and a cooperating female portion 89, as shown in FIG. 16, is permanently mounted within the interior confines of the cap and coping.

Male portion 88 has a base 88' which is preferably but not necessarily annular in shape, and also has a plurality of resilient fingers 90 extending substantially normally of the base 88'. Female portion 89 generally resembles a washer and is preferably but not necessarily circular in shape. Female portion 89 has a center opening 93. The plurality of fingers 90 together comprise a bulbous head 91 having a tapered tip to facilitate entry of the head 91 into passage 93. An annular groove 92 is formed behind the bulbous head 91 and is operative for receiving with snap-type action the wall portions of female portion 89 which bound opening 93.

Prior to permanent mounting of the fastener portions in their respective cavity or bore, the fit of the finished cap is checked in the oral cavity. The coping is removably mounted over a prepared tooth, and the cap is removably mounted over the coping. The dentist and patient now verify that the cap does not interfere with the adjacent teeth in the mouth, and that the color, size, bite, and alignment are satisfactory for the particular application.

Male portion 88 is permanently mounted to cap 79 within cavity 81 by any technique, e.g. the annular walls of the cap 79 which surround base 88' may be swaged or peened over; or adhesives or soldering techniques may be similarly employed. Preferably high energy fusion techniques, such as energy beam technology, is used to permanently weld the male portion 88 to cap 79 at weld points 94.

In a similar manner, female portion 89 is permanently welded to coping 68 within bore sections 76, 77 at weld points 95. An electron beam or a laser beam or any other high energy beam is directed at the particular welding spot and thus heats the spot to a temperature sufficient to fuse the materials located thereat.

Prior to such permanent mounting of the fastener portions, they may be peened or swaged or otherwise removably mounted in their respective cavity or bore. The fastener portions are now fitted to each other outside of the mouth in order to verify and check their mutual size, fit and retentive force characteristic.

The practitioner now applies an adhesive layer 96 over the prepared segment 17 in the patient's mouth. The adhesive layer 96 may preferably be zinc phosphate cement or epoxy resin cement. The coping 68 is installed over the cement layer 96 and is thereby permanently attached thereupon. The cap 79 is now positioned over the coping 68 and moved in translational manner such that the bulbous head 91 of male portion 88 is directed through passage 93 of female portion 89. The resilient fingers 90 are initially cammed towards each other and snap back to their original relative positions after the head 91 has cleared the passage 93. FIG. 13 shows the completed assembly in fully snapped or assembled condition.

A force on the order of 3–5 lbs. is generally required to overcome the retentive force and unsnap the assembly. An extractive force measurement is made to determine the retentive force to verify that it is adequate to securely hold the cap to the coping such that they satisfy normal and in some cases abnormal chewing and crushing operations. The resilient fingers 90 are moved towards and away from each other by tool 113 in order to adjust the retentive force by either the dentist and/or the dental laboratory.

In analogous manner, it will be understood that the cavity 81 could have been formed in coping 68, and further that the two bore sections 76, 77 could have been formed in cap 79. In that case, the male and female portions of attachment 87 would be welded to the reciprocal parts.

The coping and the interior socket of the cap are aspherical. Hence, once the cap is emplaced, the cap cannot rotate on the coping and will remain in its designated orientation.

Rather than employing the above-described male and female portions, an alternate manner of detachably fastening the cap 79 to the coping 68 is shown in FIG. 14. Magnetic button 97 having magnetic poles is friction-tightly mounted or otherwise permanently mounted in one cavity, such as cavity 81, and another magnetic button 98 having magnetic poles is similarly permanently mounted in another recess, such as bore section 76. The magnetic attraction of opposite facing poles of buttons 97 and 98 connects the cap 79 to the coping 68.

FIG. 15 shows a cap 99 mounted on a coping and on a segment 17. In this case, no recess or cavity whatsoever is formed in either the tooth segment 17 or the cap 99. Very thin, e.g. on the order of 0.005 inches, magnetic plastic or metal sheet materials 100, 101 with opposite facing poles are adhesively or otherwise attached to cap 99 and tooth segment 17.

The above-recited method has been described in connection with the prosthodontic repair of a single tooth. In another application, it is desired to span a distance of a length greater than the width of a single tooth. In such cases, a bridge structure, as identified by reference numeral 102 in FIG. 17, is employed.

Bridge 102 includes a set of crowns 103, 104, 105 and 106. These crowns are joined to one another to form an interconnected unit. Crowns 104 and 105 replace extracted teeth, and crowns 103 and 106 are detachably connected to prepared anchor teeth 107 and 108.

Anchor teeth 107 and 108 are formed with recesses 109 and 110 respectively in the manner described above for recess 35. Crowns 103 and 106 are formed with cavities 111 and 112 respectively as described above in connection with cavity 81. Detachable fastening means i.e. either the aforementioned snap-type cooperating male and female portions or the cooperating magnetic buttons or sheets are placed in or at these recesses and cavities. Thus, the bridge 102 can be detached and replaced as a unit.

The male and female snap-type portions 88, 89 are preferably dimensioned in a plurality of sizes, e.g. small, medium, and large in dependence upon the size and type of the tooth to be repaired. The dimensions of the cavity and of the bore sections of course correspond to the selected sizes of the male and female portions. For example, larger bore section 76 may be dimensioned in inches (mm) as 0.1180 (3.00), or 0.0906 (2.30) or 0.065 (1.65); and smaller bore section 77 may be dimensioned in inches (mm) as 0.0906 (2.3) or 0.0591 (1.5) or 0.0413 (1.05). The invention is not intended to be limited to these dimensions; these dimensions are given merely to show the miniaturization of the various fastener parts.

The metals used for the male and female snap fastener parts are preferably corrosion-resistant to the action of acids and alkalis which generally exist in the oral cavity. These metals are resilient and preferably have a high fatigue range and do not appreciably distort or creep under stress with time. These metals are easily weldable, solderable, cementable, and capable of being easily handled and manipulated. An example of one such suitable alloy has the following characteristics:

| | |
|---|---|
| Ultimate Tensile Stress Strength (psi) | 300,000–360,000 |
| Yield Stress (psi) | 250,000–280,000 |
| Proportional Limit (psi) | 200,000–230,000 |
| Elastic Modulus | 29.5 million |
| Hardness (RC) | 55–59 |

The alloy is preferably coldworked up to 85%. The degree of coldworking affects all of its physical properties, particularly its resilience.

An alloy having such characteristics has been fabricated and has

| | |
|---|---|
| Carbon | 0.05 – 0.10% |
| Manganese | 2.0 – 2.5% |
| Chromium | 17.0% – 18.0% |
| Nickel | 17.0% – 18.0% |
| Cobalt | 47.0% – 48% |
| Molybdenum | 6.0% – 7% |
| Iron | Balance |

Any commercially available alloy or metal meeting the above physical properties is suitable for the type of fasteners described herein.

Some metals in common use in dentistry for caps and copings are strong, corrosion-resistant and extremely hard. Such properties make them difficult to drill, tap, stamp, roll or otherwise fabricate. In accordance with the invention, the fusion technique discussed above is very well suited for such metals and permits a simple and economical manufacture.

It will be understood that each of the elements described above, or two or more together, may also find a useful application in other types of constructions differing from the types described above.

While the invention has been illustrated and described as embodied in a detachable mount for a dental cap and prosthodontic method utilizing the same, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A prosthetic method of repairing a tooth, comprising the steps of:
   (a) preparing a tooth to be repaired;
   (b) forming an elongated recess in the prepared tooth;
   (c) providing a coping for placement over the prepared tooth;
   (d) forming the coping with a bore which extends in direction of the elongation of the recess;
   (e) providing a cap for placement over the coping by inserting a stud into said bore for a depth such that a trailing portion of the stud projects for a predetermined distance outwardly beyond the coping, applying a hardenable substance about the exterior of said projecting portion and the coping, and substituting cap material for said hardened substance, thereby to form a cap;
   (f) forming the cap with a cavity which extends in direction of the elongation of the recess;
   (g) mounting one part of a two-part detachable fastener in said bore of said coping;
   (h) mounting another part of a two-part detachable fastener in said cavity of said cap; and
   (i) moving said parts along said direction into engagement with each other to thereby fasten the cap to the coping free of relative misalignment due to the mutual alignment of the bore and the cavity.

2. The prosthetic method of claim 1, wherein said step of forming the cap with the cavity includes the step of directing a material-removing tool towards the interior of the cap in direction along the elongation of the recess, and thereby forming the cavity in the region of the cap formerly occupied by said projecting portion.

3. In an arrangement for repairing teeth, a combination comprising:
   (a) means for preparing a tooth to be repaired;
   (b) means for forming an elongated recess in the prepared tooth;
   (c) means for forming a coping for placement over the prepared tooth, said coping having a bore which extends in direction of the elongation of the recess;
   (d) means for forming a cap for placement over the coping, said cap having an elongated cavity;
   (e) means for aligning the cavity to extend in direction of the elongation of the recess; and
   (f) detachable fastening means for securing the cap to the coping free of relative misalignment, said fastening means having a first part including a base and a plurality of resilient fingers extending transversely of the base, and a second part including wall portions bounding an opening, one of said parts being permanently connected to said cap within said cavity and the other of said parts being mounted in the bore of the coping, said parts being operative for connection with each other with snap-type action and with freedom of misalignment due to the mutual alignment of the bore and cavity.

4. The arrangement of claim 3, wherein said first part further includes a bulbous head insertable through said opening, and an annular groove for snappingly engaging said wall portions bounding said opening upon full insertion.

5. A prosthetic method of repairing a tooth, comprising the steps of:
 (a) preparing a tooth to be repaired;
 (b) forming an elongated recess in the prepared tooth by forming a mold having a model form substantially duplicating the configuration of the prepared tooth, marking the model form with a substantially vertical line, forming a transparent envelope over the model form, marking the transparent envelope with a mark corresponding to the vertical line, positioning the marked envelope over the prepared tooth and directing a tooth structure removing tool in the direction of elongation of said guide line;
 (c) providing a coping for placement over the prepared tooth;
 (d) forming the coping with a bore which extends in direction of the elongation of the recess;
 (e) providing a cap for placement over the coping;
 (f) forming the cap with a cavity which extends in direction of the elongation of the recess;
 (g) mounting one part of a two-part detachable fastener in said bore of said coping;
 (h) mounting another part of a two-part detachable fastener in said cavity of said cap; and
 (i) moving said parts along said direction into engagement with each other to thereby fasten the cap to the coping free of relative misalignment due to the mutual alignment of the bore and the cavity.

6. A prosthetic method of repairing a tooth, comprising the steps of:
 (a) preparing a tooth to be repaired;
 (b) forming an elongated recess in the prepared tooth;
 (c) providing a coping for placement over the prepared tooth by forming a mold having a model form which substantially duplicates the configuration of the prepared tooth formed with said recess, applying a hardenable substance over said model form, controlling the thickness of the hardenable substance located in said recess and substituting coping material for the hardened substance, thereby to form a coping;
 (d) forming the coping with a bore which extends in in direction of the elongation of the recess;
 (e) providing a cap for placement over the coping;
 (f) forming the cap with a cavity which extends in direction of the elongation of the recess;
 (g) mounting one part of a two-part detachable fastener in said bore of said coping;
 (h) mounting another part of a two-part detachable fastener in said cavity of said cap; and
 (i) moving said parts along said direction into engagement with each other to thereby fasten the cap to the coping free of relative misalignment due to the mutual alignment of the bore and the cavity.

7. A prosthetic method of repairing a tooth, comprising the steps of:
 (a) preparing a tooth to be repaired;
 (b) forming an elongated recess in the prepared tooth;
 (c) providing a coping for placement over the prepared tooth;
 (d) forming the coping with a bore which extends in the direction of the elongation of the recess by directing a rotary material removing tool having cutting portions of different diameters toward said coping in the direction along the elongation of the recess and thereby forming a pair of bore sections corresponding to said diameters;
 (e) providing a cap for placement over the coping;
 (f) forming the cap with a cavity which extends in direction of the elongation of the recess;
 (g) mounting one part of a two-part detachable fastener in said bore of said coping;
 (h) mounting another part of a two-part detachable fastener in said cavity of said cap; and
 (i) moving said parts along said direction into engagement with each other to thereby fasten the cap to the coping free of relative misalignment due to the mutual alignment of the bore and the cavity.

8. A prosthetic method of repairing a tooth, comprising the steps of:
 (a) preparing a tooth to be repaired;
 (b) forming an elongated recess in the prepared tooth;
 (c) providing a coping for placement over the prepared tooth;
 (d) forming the coping with a bore which extends in direction of the elongation of the recess;
 (e) providing a cap for placement over the coping;
 (f) forming the cap with a cavity which extends in direction of the elongation of the recess;
 (g) mounting one part of a two-part detachable fastener in said bore of said coping by a fusion welding step; p1 (h) mounting another part of a two-part detachable fastener in said cavity of said cap by a fusion welding step;
 (i) moving said parts along said direction into engagement with each other to thereby fasten the cap to the coping free of relative misalignment due to the mutual alignment of the bore and the cavity.

9. A prosthetic method of repairing a tooth, comprising the steps of:
 (a) preparing a tooth to be repaired;
 (b) forming an elongated recess in the prepared tooth;
 (c) providing a coping for placement over the prepared tooth by forming a mold having a model form which substantially duplicates the configuration of the prepared tooth formed with said recess, applying a hardenable substance over said model form, controlling the thickness of the hardenable substance located in said recess and substituting coping material for the hardened substance, thereby to form a coping;
 (d) forming the coping with a bore which extends in direction of the elongation of the recess;
 (e) providing a cap for placement over the coping;
 (f) forming the cap with a cavity which extends in direction of the elongation of the recess;
 (g) mounting one part of a two-part detachable magnetic fastener in said bore of said coping, with one pole of said magnet facing outwardly;
 (h) mounting the other part of said two-part detachable magnetic fastener in said cavity of said cap, with the pole of opposite polarity to the outermost facing pole of said one part directed outwardly;

(i) moving said parts along said direction into engagement with each other, thereby magnetically to fasten the cap to the coping free of relative misalignment due to the mutual alignment of the bore and the cavity.

10. In an arrangement for repairing teeth, a combination comprising:
   (a) means for preparing a tooth to be repaired, said preparing means including a marking tool having means for slidably bearing against a major surface of the tooth and means for marking another major surface of the tooth during such sliding movement;
   (b) means for forming an elongated recess in the prepared tooth;
   (c) means for forming a coping for placement over the prepared tooth, said coping having a bore which extends in direction of the elongation of the recess; p1 (d) means for forming a cap for placement over the coping, said cap having an elongated cavity;
   (e) means for aligning the cavity to extend in direction of the elongation of the recess; and
   (f) detachable fastening means for securing the cap to the coping free of relative misalignment, said fastening means having one part mounted in the cavity of the cap, and another part mounted in the bore of the coping and operative for receiving said one part with snap-type action and with freedom of misalignment due to the mutual alignment of the bore and the cavity.

11. In an arrangement for repairing teeth, a combination comprising:
   (a) means for preparing a tooth to be repaired;
   (b) means for forming an elongated recess in the prepared tooth;
   (c) means for forming a coping for placement over the prepared tooth, said coping having a bore which extends in the direction of the elongation of the recess, said coping forming means including means for controlling the thickness of the coping in the region of said bore, said controlling means including a sleeve and a depth rod mounted for sliding movement relative to said sleeve;
   (d) means for forming a cap for placement over the coping, said cap having an elongated cavity;
   (e) means for aligning the cavity to extend in direction of the elongation of the recess; and
   (f) detachable fastening means for securing the cap to the coping free of relative misalignment, said fastening means having one part mounted in the cavity of the cap, and another part mounted in the bore of the coping and operative for receiving said one part with snap-type action and with freedom of misalignment due to the mutual alignment of the bore and the cavity.

12. In an arrangement for repairing teeth, a combination comprising:
   (a) means for preparing a tooth to be repaired;
   (b) means for forming an elongated recess in the prepared tooth;
   (c) means for forming a coping for placement over the prepared tooth, said coping having a bore which extends in direction of the elongation of the recess;
   (d) means for forming a cap for placement over the coping, said cap having an elongated cavity;
   (e) means for aligning the cavity to extend in the direction of the elongation of the recess, said aligning means including a stud insertible into said bore, said stud having a leading portion mounted in said bore and a trailing portion projecting outwardly beyond said coping; and
   (f) detachable fastening means for securing the cap to the coping free of relative misalignment, said fastening means having one part mounted in the cavity of the cap, and another part mounted in the bore of the coping and operative for receiving said one part with snap-type action and with freedom of misalignment due to the mutual alignment of the bore and the cavity.

13. In an arrangement for repairing teeth, a combination comprising:
   (a) means for preparing a tooth to be repaired;
   (b) means for forming an elongated recess in the prepared tooth;
   (c) means for forming a coping for placement over the prepared tooth, said coping having a bore which extends in the direction of the elongation of the recess, said coping forming means including means for controlling the thickness of the coping in the region of said bore, said controlling means including a sleeve and a depth rod mounted for sliding movement relative to said sleeve;
   (d) means for forming a cap for placement over the coping, said cap having an elongated cavity;
   (e) means for aligning the cavity to extend in direction of the elongation of the recess; and
   (f) detachable fastening means for securing the cap to the coping free of relative misalignment, said fastening means having a first part comprising a permanent magnet mounted in the cavity of the cap and a second part comprising a permanent magnet mounted in the bore of the coping, said magnetic parts being aligned in said cavity and bore to lie in juxtaposition when said cap is seated on said coping, said fastening means, in said juxtaposed position, having poles of opposite polarity facing each other whereby said cap is held to said coping with freedom of misalignment due to the mutual alignment of the bore and the cavity.

* * * * *